US012433979B2

(12) United States Patent
Norman et al.

(10) Patent No.: US 12,433,979 B2
(45) Date of Patent: Oct. 7, 2025

(54) PERITONEAL DIALYSIS PATIENT LINE WITH STERILIZING FILTER AND DRAIN BYPASS

(71) Applicants: BAXTER INTERNATIONAL INC., Deerfield, IL (US); BAXTER HEALTHCARE SA, Glattpark (CH)

(72) Inventors: John Norman, Gurnee, IL (US); Edward Szpara, St. Charles, IL (US); Karl Cazzini, Lindenhurst, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 254 days.

(21) Appl. No.: 17/984,704

(22) Filed: Nov. 10, 2022

(65) Prior Publication Data

US 2023/0073788 A1 Mar. 9, 2023

Related U.S. Application Data

(63) Continuation of application No. 16/574,756, filed on Sep. 18, 2019, now Pat. No. 11,511,025.

(Continued)

(51) Int. Cl.
*A61M 1/16* (2006.01)
*A61M 1/14* (2006.01)
*A61M 1/28* (2006.01)

(52) U.S. Cl.
CPC ........ *A61M 1/1645* (2014.02); *A61M 1/1524* (2022.05); *A61M 1/155* (2022.05);

(Continued)

(58) Field of Classification Search
CPC .............. A61M 1/1645; A61M 1/1672; A61M 1/1686; A61M 1/28; A61M 1/284;

(Continued)

(56) References Cited

U.S. PATENT DOCUMENTS 4,311,587 A 1/1982 Nose et al.
6,129,699 A 10/2000 Haight et al.

(Continued)

FOREIGN PATENT DOCUMENTS

EP 0928615 7/1999
EP 3466461 4/2019

OTHER PUBLICATIONS

IPRP—PCT/US2019/051685 dated Mar. 24, 2020—1 page.

(Continued)

*Primary Examiner* — Dirk R Bass
(74) *Attorney, Agent, or Firm* — K&L Gates LLP

(57) ABSTRACT

A medical fluid treatment system includes a source of purified water; at least one concentrate for mixing with the water from the source to form a treatment fluid; a disposable set including a pumping portion, a concentrate line in fluid communication with the concentrate source and the pumping portion, and a patient line in fluid communication with the pumping portion, the patient line including a filter having a membrane configured to filter the treatment fluid, the filter configured such that (i) fresh treatment fluid flowing from the pumping portion towards a patient flows through the membrane and (ii) used treatment fluid flowing through the filter from the patient to the pumping portion bypasses the membrane; and a medical fluid delivery machine including a pump actuator operable with the pumping portion of the disposable set.

19 Claims, 5 Drawing Sheets

Related U.S. Application Data

(60) Provisional application No. 62/732,782, filed on Sep. 18, 2018.

(52) U.S. Cl.
CPC ........ *A61M 1/1561* (2022.05); *A61M 1/1565* (2022.05); *A61M 1/159* (2022.05); *A61M 1/1672* (2014.02); *A61M 1/1686* (2013.01); *A61M 1/285* (2013.01); *A61M 1/288* (2014.02); *A61M 1/284* (2014.02); *A61M 2205/126* (2013.01); *A61M 2205/3331* (2013.01); *A61M 2205/502* (2013.01)

(58) Field of Classification Search
CPC .................. A61M 1/285; A61M 1/288; A61M 2205/126; A61M 2205/3331; A61M 2205/502; A61M 2205/7509; A61M 2205/7518; A61M 2205/7545
See application file for complete search history.

(56) References Cited

U.S. PATENT DOCUMENTS

| | | | |
|---|---|---|---|
| 6,758,971 | B1 | 7/2004 | Haight |
| 2016/0038666 | A1 | 2/2016 | Kelly et al. |
| 2018/0043081 | A1 | 2/2018 | Lura et al. |

OTHER PUBLICATIONS

Written Opinion—PCT/US2019/051685 dated Mar. 24, 2020—11 pages.
International Search Report—PCT/US2019/051685 dated Mar. 24, 2020—5 pages.

PERITONEAL DIALYSIS PATIENT LINE WITH STERILIZING FILTER AND DRAIN BYPASS

RELATED APPLICATIONS

This application claims priority to and the benefit as a continuation of U.S. patent application Ser. No. 16/574,756, filed Sep. 18, 2019, now U.S. Pat. No. 11,511,025, entitled "PERITONEAL DIALYSIS PATIENT LINE WITH STERILIZING FILTER AND DRAIN BYPASS", which claims the benefit of and priority to U.S. Provisional Patent Application No. 62/732,782 filed Sep. 18, 2018, having the same title, the entire contents of each of which are incorporated herein by reference and relied upon.

BACKGROUND

The present disclosure relates generally to medical fluid devices. More specifically, the present disclosure relates to medical fluid devices that mix fluid online for treatment or that receive fluid mixed online for treatment.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney function is critical to many people because the treatment is life saving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three day's worth of toxins prior to a treatment. In certain areas, the closest dialysis center may be many miles from the patient's home, causing door-to-door treatment time to consume a large portion of the day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" may occur at the end of the APD treatment. The fluid may remain in the peritoneal cavity of the patient until the start of the next treatment, or may be manually emptied at some point during the day.

In any of the above modalities using an automated machine, treatment fluid may be prepared online or at the point of use, e.g., before and/or during the treatment. It is important that the fluid is properly purified before being used for treatment or delivered to the patient. A need exists accordingly for an improved online or at the point of use system that ensures the fluid being prepared is of a sufficient quality.

SUMMARY

The examples described herein disclose automated systems and methods applicable, for example, to fluid delivery for: peritoneal dialysis ("PD"), plasmapheresis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. The systems and methods described herein are applicable to any medical fluid delivery system in which the treatment fluid may be made online or at the point of use, e.g., just before and/or during treatment. These modalities may be referred to collectively or generally individually herein as medical fluid delivery system(s).

Moreover, each of the systems and methods described herein may be used with clinical or home-based treatments. For example, the present systems and methods may be employed in in-center PD, HD, HF or HDF machines, which run throughout the day. Alternatively, the present systems and methods may be used with home PD, HD, HF or HDF machines, which are operated generally at the patient's convenience.

In one embodiment, a peritoneal dialysis system and method are provided having point of use dialysis fluid production. The system includes a cycler and a water purifier. The cycler includes a control unit having at least one processor and at least one memory. The cycler may further include a wired or wireless transceiver for sending information to and receiving information from the water purifier. The water purifier may also include a control unit having at least one processor and at least one memory and a wired or wireless transceiver for sending information to and receiving information from the control unit of the cycler.

The cycler includes equipment programmed via its control unit to prepare fresh dialysis solution at the point of use, pump the freshly prepared dialysis fluid to a patient, allow the dialysis fluid to dwell within the patient, then pump used dialysis fluid to a drain. The cycler in one embodiment includes a heater under control of the control unit for heating the dialysis fluid as it is being mixed. The heater may for example be located at the top of a housing of the cycler, e.g., beneath a heating lid.

The cycler (and the water purifier in one embodiment) operates with a disposable set. The disposable set may include a disposable pumping cassette, which may be constructed of a planar rigid plastic piece covered on one or both sides by a flexible membrane, forming fluid pumping and valving chambers. The fluid pump chambers may operate with pneumatic pump chambers of the cycler, while fluid valve chambers operate with the pneumatic valve chambers of the cycler.

The disposable set may include (i) a patient line that extends from the cassette to a patient line connector, (ii) a drain line that extends from the cassette to a drain line connector (which may in turn connect removeably to the water purifier), (iii) a heater/mixing line that extends from the pumping cassette to a heater/mixing bag of the present disclosure, (iv) an upstream water line segment that extends from the water purifier to a water inlet of a water accumulator and a downstream water line segment that extends from a water outlet of the water accumulator to the cassette, (v) a last bag or sample line that extends from the cassette to a premixed last fill bag of dialysis fluid or to a sample bag or other sample collecting container, (vi) a first, e.g., glucose, concentrate line extending from the cassette to a first, e.g., glucose, concentrate container, and/or (vii) a second, e.g., buffer, concentrate line that extends from the cassette to a second, e.g., buffer, concentrate container.

A patient line of the present disclosure connects in one embodiment to a single lumen catheter extending into the peritoneal cavity of the patient. During treatment, fresh peritoneal dialysis fluid is infused through the catheter into the patient's peritoneal cavity and allowed to dwell for a period of time, e.g., about four hours. During that time period, toxins migrate osmotically through the patient's peritoneal wall, which lines the patient's peritoneal cavity, into the dialysis fluid removing the toxins from the patient's blood. Used dialysis fluid (also called an effluent) is then drained back through the patient line and discarded. If the dialysis solution contains contaminates upon the infusion, the patient can experience complications. One source of contaminates occurs upon making tubing connections with the disposable set, e.g., when the patient or caregiver touches the connections and/or does not properly disinfect the connectors upon disconnection.

To combat the above-described contaminants, it is contemplated to place a filter in the patient line, along the single lumen passageway, which filters the dialysis solution prior to being infused into the patient. The filter is provided in a housing that causes used dialysis fluid or effluent drained from the patient through the same patient line to bypass a filter membrane of the filter to prevent (i) clogging of the filter and (ii) the filter from filtering out toxins or other substances from the effluent, which may then be reinfused back into the patient along with fresh dialysis fluid in the next infusion cycle through the same patient line.

In one embodiment, the filter housing is configured so that parallel fluid pathways are created within the housing. A fresh dialysis fluid pathway through one or more membrane of the filter is provided to deliver filtered fresh dialysis fluid to the patient. Used dialysis fluid on the other hand flows through the filter housing via a different, parallel pathway, which bypasses the one or more membrane of the filter. In one embodiment, the parallel pathways are aided using a pair of one-way or check valves (such as duckbill check valves). A first one-way valve is placed at a fresh dialysis fluid exit end of the fresh dialysis fluid pathway of the housing. The first check valve is oriented to block incoming used dialysis fluid and to allow fresh dialysis fluid flowing through the fresh dialysis fluid pathway to exit the filter housing and flow to the patient. A second one-way valve is placed at a used dialysis fluid exit end of the used dialysis fluid pathway of the housing. The second one-way valve is oriented to block incoming fresh dialysis fluid and to allow used dialysis fluid flowing through the used dialysis fluid pathway to exit the filter housing and flow to a pumping cassette of the disposable set, from which it is pumped to drain.

Fresh dialysis fluid flowing through the fresh dialysis fluid pathway flows in one embodiment through an inline membrane housing. The membrane housing may include a spacer having a rectangular grid of passageways that extend vertically from upper and lower exterior membrane surfaces into a rectangular gap passageway located adjacent to the grid, wherein the gap leads to an exit pathway of the filter housing. In one embodiment, the filter membranes are hydrophilic materials having micropores that allow purified fluid to pass but that trap contaminants. When the hydrophilic filter membranes are wetted, the membranes prevent the passage of air.

In one embodiment, two rectangular filter membranes are sealed to form upper and lower surfaces, respectively, of the membrane housing. Fresh fluid enters the filter and then divides into two fresh dialysis fluid streams or branches, one stream or branch flowing over the top of the upper membrane and another stream or branch flowing below the bottom of the lower filter membrane. The upper stream flows downwardly through the upper membrane into the spacer grid, then out the exit pathway of the filter housing, through the one-way valve to the patient. The lower stream flows upwardly through the lower membrane into the spacer grid of the membrane housing, then out the exit pathway of the filter, through the fresh dialysis fluid one-way valve to the patient. The same fresh fluid check valve is oriented to prevent used dialysis fluid exiting the patient from flowing back the other way through the filter membranes. The used dialysis fluid pathway instead bypasses the membrane housing altogether.

At the end of a patient dwell phase, the dialysis machine or cycler supplies a negative pressure along the patient line to pull used dialysis fluid from the patient. Again, the check valve at the end of the fresh dialysis fluid path prevents effluent from flowing into the interior region of the membrane housing and out through the membranes. Instead, the one-way valve diverts the effluent to bypass the filter membranes and flow instead along the used dialysis fluid pathway formed within the filter housing, which extends alongside the membrane housing. Effluent flow is directed to the pumping cassette as mentioned above.

The filter structure just described leads to a filtration method, which includes preparing a medical solution, such as dialysis solution for treatment, delivering the treatment fluid along a patient line through a filter membrane to a patient, and returning used solution through the same patient line but bypassing the filter membrane. In the method, bypassing the filter membrane may include doing so while still flowing the used solution through an overall housing of the filter.

Placing the sterilizing filter in the patient line has a number of advantages. First, the location is just prior to the medical fluid reaching the patient, so that any contaminants residing in the disposable set, e.g., due to set condition, except for contaminants located in the short section of tubing leading from the filter to the patient, will be removed from the medical fluid. Second, the filter is located post-mixing, so the filter will remove any contaminants provided via one or more concentrate used to create the online medical fluid. Third, there is likely to be a clean, unobstructed portion of the patient line extending from a pump or pressure providing portion of the disposable set to the filter, making a pressure test of the filter membranes prior to delivery to the patient readily available.

It should be appreciated that although the thrust of the present disclosure is described in connection with peritoneal dialysis, the present disclosure is applicable to other medical fluid applications in which an infused or treatment solution is to be devoid of contaminants as much as possible, such as other types of dialysis applications, a substitution fluid application or an intravenous ("IV") infusion pump application.

In light of the disclosure herein and without limiting the disclosure in any way, in a first aspect of the present disclosure, which may be combined with any other aspect listed herein unless specified otherwise, a dialysis system includes: a medical fluid treatment system includes: a source of purified water; at least one concentrate for mixing with the water from the source to form a treatment fluid; a disposable set including a pumping portion, a concentrate line in fluid communication with the concentrate source and the pumping portion, and a patient line in fluid communication with the pumping portion, the patient line including a filter having a membrane configured to filter the treatment fluid, the filter configured such that (i) fresh treatment fluid flowing from the pumping portion towards a patient flows through the membrane and (ii) used treatment fluid flowing through the filter from the patient to the pumping portion bypasses the membrane; and a medical fluid delivery machine including a pump actuator operable with the pumping portion of the disposable set.

In a second aspect of the present disclosure, which may be combined with any other aspect listed herein unless specified otherwise, wherein the treatment fluid is a peritoneal dialysis treatment fluid.

In a third aspect of the present disclosure, which may be combined with any other aspect listed herein unless specified otherwise, the filter includes a fresh treatment fluid pathway and a used treatment fluid pathway placed in parallel with the fresh treatment fluid pathway, the membrane located along the fresh fluid pathway, the used treatment fluid pathway enabling the used treatment fluid flowing through the filter to bypass the membrane.

In a fourth aspect of the present disclosure, which may be combined with the third aspect in combination with any other aspect listed herein unless specified otherwise, a one-way valve is located at an exit end of the fresh treatment fluid pathway, the one-way valve positioned and arranged to prevent used treatment fluid returning from the patient from reaching the membrane.

In a fifth aspect of the present disclosure, which may be combined with the third aspect in combination with any other aspect listed herein unless specified otherwise, a one-way valve is located at an exit end of the used treatment fluid pathway, the one-way valve positioned and arranged to prevent fresh treatment fluid flowing through the filter via the used treatment fluid pathway.

In a sixth aspect of the present disclosure, which may be combined with the third aspect in combination with any other aspect listed herein unless specified otherwise, the membrane is housed in a membrane housing located along the fresh fluid pathway, and wherein the filter is configured such that fresh treatment fluid flows from outside the membrane housing, through the membrane, and into an interior region of the membrane housing.

In a seventh aspect of the present disclosure, which may be combined with the third aspect in combination with any other aspect listed herein unless specified otherwise, the filter includes a housing having a first port and a second port, the first port opening to a first end of the filter housing and the second port opening to a second end of the filter housing, the first end of the filter housing forming a first end of the fresh and used treatment fluid pathways, and the second end of the filter housing forming a second end of the fresh and used treatment fluid pathways.

In an eighth aspect of the present disclosure, which may be combined with the seventh aspect in combination with any other aspect listed herein unless specified otherwise, the first end of the fresh fluid treatment pathway at the first end of the filter housing includes a first one-way valve, and wherein the second end of the used fluid treatment pathway at the second end of the filter housing includes a second one-way valve.

In a ninth aspect of the present disclosure, which may be combined with any other aspect listed herein unless specified otherwise, the membrane is housed in a membrane housing, and wherein fresh treatment fluid entering the filter flows to an outside of the membrane housing, and fresh treatment fluid exiting the filter flows from an inside of the membrane housing.

In a tenth aspect of the present disclosure, which may be combined with any other aspect listed herein unless specified otherwise, the membrane is a first membrane, and wherein the filter includes a second membrane, wherein the first and second membranes are housed in a membrane housing, and wherein fresh treatment fluid entering the filter is split into a first branch flowing to an outside of the first membrane and a second branch flowing to an outside of the second membrane.

In an eleventh aspect of the present disclosure, which may be combined with the tenth aspect in combination with any other aspect listed herein unless specified otherwise, the membrane housing includes a grid of passageways located between the first and second membranes.

In a twelfth aspect of the present disclosure, which may be combined with the tenth aspect in combination with any other aspect listed herein unless specified otherwise, the first and second membranes are located on opposing sides of the membrane housing, respectively, the first branch extending to a first side of the housing and the second branch extending to a second side of the housing.

In a thirteenth aspect of the present disclosure, which may be combined with any other aspect listed herein unless specified otherwise, (i) the pump actuator operable with the pumping portion of the medical fluid delivery machine includes a pneumatic pump actuator and the pumping portion of the disposable set includes a pumping membrane or (ii) the pump actuator operable with the pumping portion of the medical fluid delivery machine includes a peristaltic pump actuator and the pumping portion of the disposable set includes a peristaltic pumping tube.

In a fourteenth aspect of the present disclosure, which may be combined with any other aspect listed herein unless specified otherwise, the medical fluid treatment system includes at least one hydrophobic vent for removing air from the filter.

In a fifteenth aspect of the present disclosure, which may be combined with any other aspect listed herein unless specified otherwise, a disposable set for a medical fluid treatment system includes: a pumping portion; a concentrate line in fluid communication with the pumping portion; and a patient line in fluid communication with the pumping portion, the patient line including a filter having a membrane configured to filter the treatment fluid, the filter configured such that (i) fresh treatment fluid flowing from the pumping portion towards a patient flows through the membrane and (ii) used treatment fluid flowing through the filter from the patient to the pumping portion bypasses the membrane via a one-way valve that is positioned and arranged to open under fresh treatment fluid pressure and close under used treatment fluid pressure.

In a sixteenth aspect of the present disclosure, which may be combined with the fifteenth aspect in combination with any other aspect listed herein unless specified otherwise, the one-way valve includes a duckbill check valve.

In a seventeenth aspect of the present disclosure, which may be combined with the fifteenth aspect in combination with any other aspect listed herein unless specified otherwise, the one-way valve is a first one-way valve, and which includes a second one-way valve positioned at a second end of the filter opposing a first end of the filter in which the first one-way valve is positioned, the second one-way valve positioned and arranged to open under used treatment fluid pressure and close under fresh treatment fluid pressure.

In an eighteenth aspect of the present disclosure, which may be combined with any other aspect listed herein unless specified otherwise, a filter in which fluid is intended to flow in first and second directions, wherein the filter is configured to filter fluid flowing in the first direction and to not filter fluid flowing in the second direction, includes: a housing; a first fluid pathway provided by the housing for flowing fluid in the first direction; a second fluid pathway provided by the housing for flowing fluid in the second direction; a membrane positioned to filter the fluid flowing in the first direction; and a one-way valve located at an exit end of the first fluid pathway, the one-way valve positioned and arranged to prevent fluid flowing in the second direction from reaching the membrane.

In a nineteenth aspect of the present disclosure, which may be combined with the eighteenth aspect in combination with any other aspect listed herein unless specified otherwise, the filter is part of a disposable set including a fluid line connected to the filter and a pumping portion for operation with a pump actuator, the pumping portion in fluid communication with the fluid line.

In a twentieth aspect of the present disclosure, which may be combined with the nineteenth aspect in combination with any other aspect listed herein unless specified otherwise, the pumping portion is part of a disposable cassette of the disposable set, the fluid line extending from the disposable cassette to the filter.

In a twenty-first aspect of the present disclosure, which may be combined with the nineteenth aspect in combination with any other aspect listed herein unless specified otherwise, the filter is configured to fluidly communicate the fluid line at different times with the first fluid pathway and the second fluid pathway of the filter.

In a twenty-second aspect of the present disclosure, which may be combined with the nineteenth aspect in combination with any other aspect listed herein unless specified otherwise, the fluid line is a first fluid line, and wherein the disposable set includes a second fluid line connected to the filter, the second fluid line for extending to a fluid delivery destination.

In a twenty-third aspect of the present disclosure, which may be combined with the eighteenth aspect in combination with any other aspect listed herein unless specified otherwise, the one-way valve is a first one-way valve, and which includes a second one-way valve located at an exit end of the second fluid pathway, the second one-way valve positioned and arranged to prevent fluid flowing in the first direction from flowing through the second fluid pathway.

In a twenty-fourth aspect of the present disclosure, which may be combined with the twenty-third aspect in combination with any other aspect listed herein unless specified otherwise, the housing includes (i) a first port located downstream from the first one-way valve and in fluid communication with the second fluid pathway and (ii) a second port located downstream from the second one-way valve and in fluid communication with the first fluid pathway.

In a twenty-fifth aspect of the present disclosure, which may be combined with the eighteenth aspect in combination with any other aspect listed herein unless specified otherwise, the membrane is housed in a membrane housing located within the filter housing and along the first fluid pathway, and wherein the filter housing is configured such that fluid flowing in the first direction flows from outside of the membrane housing, through the membrane, and into an interior region of the membrane housing.

In a twenty-sixth aspect of the present disclosure, which may be combined with the twenty-fifth aspect in combination with any other aspect listed herein unless specified otherwise, fluid flowing in the first direction exits the filter from the interior region of the membrane housing and fluid flowing in the second direction bypasses the membrane housing via the second fluid pathway.

In a twenty-seventh aspect of the present disclosure, which may be combined with the twenty-fifth aspect in combination with any other aspect listed herein unless specified otherwise, the membrane is a first membrane and which includes a second membrane, wherein the first and second membranes are housed in the membrane housing, and wherein fluid flowing in the first direction is split into a first branch flowing to an outside of the first membrane and a second branch flowing to an outside of the second membrane.

In a twenty-eighth aspect of the present disclosure, which may be combined with the twenty-seventh aspect in combination with any other aspect listed herein unless specified otherwise, the membrane housing includes a grid of passageways located between the first and second membranes.

In a twenty-ninth aspect of the present disclosure, which may be combined with the twenty-seventh aspect in combination with any other aspect listed herein unless specified otherwise, the first and second membranes are located on opposing sides of the membrane housing, respectively, the first branch extending to a first side of the membrane housing and the second branch extending to a second side of the membrane housing.

In a thirtieth aspect of the present disclosure, which may be combined with the eighteenth aspect in combination with any other aspect listed herein unless specified otherwise, the housing includes a hydrophobic vent for air removal.

In a thirty-first aspect of the present disclosure, which may be combined with any other aspect listed herein unless specified otherwise, a medical fluid treatment method includes: enabling preparation of a medical fluid at a point of use for treatment; enabling delivery of the medical fluid along a patient line through a filter membrane to a patient; and enabling return of used medical fluid through the same patient line in which the filter membrane is bypassed.

In a thirty-second aspect of the present disclosure, which may be combined with the thirty-first aspect in combination with any other aspect listed herein unless specified otherwise, the filter membrane and the bypass occur within a filter housing the filter membrane.

In a thirty-third aspect of the present disclosure, which may be combined with the thirty-first aspect in combination with any other aspect listed herein unless specified otherwise, the medical fluid prepared at the point of use for treatment is a peritoneal dialysis fluid.

In a thirty-fourth aspect of the present disclosure, which may be combined with any other aspect listed herein unless specified otherwise, a fluid filtering method includes: enabling fluid flowing from a first port of a filter to a second port of the filter to be filtered; and enabling fluid flowing from the second port of the filter to the first port of the filter to bypass filtration.

In a thirty-fifth aspect of the present disclosure, which may be combined with the thirty-fourth aspect in combination with any other aspect listed herein unless specified otherwise, enabling fluid flowing from the second port of the filter to the first port of the filter to bypass filtration includes diverting fluid flowing from the second port of the filter to the first port away from a filtration mechanism.

In a thirty-sixth aspect of the present disclosure, which may be combined with the thirty-fourth aspect in combination with any other aspect listed herein unless specified otherwise, the method further includes enabling fluid flowing from the first port of the filter to the second port of the filter to bypass a fluid pathway used by fluid flowing from the second port of the filter to the first port of the filter.

In a thirty-seventh aspect of the present disclosure, any of the structure, functionality and alternatives disclosed in connection with FIGS. 1 to 6 may be combined with any of the other structure, functionality and alternatives disclosed in connection with FIGS. 1 to 6.

In light of the present disclosure and the above aspects, it is therefore an advantage of the present disclosure to provide an improved medical fluid delivery system.

It is another advantage of the present disclosure to provide an improved medical fluid delivery system that prepares treatment fluid online or at the point of use.

It is yet another advantage of the present disclosure to provide an improved medical fluid delivery system having a sterile sterilizing grade filter in the patient line.

It is yet a further advantage of the present disclosure to provide an improved medical fluid delivery system having a sterile sterilizing grade filter that filters mixed online treatment fluid.

It is yet another advantage of the present disclosure to provide an improved medical fluid delivery system having a sterile sterilizing grade filter that is readily accessible to be purged of air and primed with liquid.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

The examples described herein are applicable to any medical fluid therapy system that delivers a medical fluid that may be mixed at the point of use, prior to and/or during treatment, such as dialysis fluid, substitution fluid, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines described herein may be used in clinical or home settings. For example, the machines and associated methods may be employed in an in-center PD or HD machine, which runs virtually continuously throughout the day. Alternatively, the machine and methods may be used in a home PD or HD machine, which can for example be run at night while the patient is sleeping. The machines and methods discussed herein are also applicable to medical delivery applications. The following examples will be described in the setting of a peritoneal dialysis system having point of use dialysis fluid production but may instead be used to make point of use treatment fluid for any of the above modalities.

Figure 1:
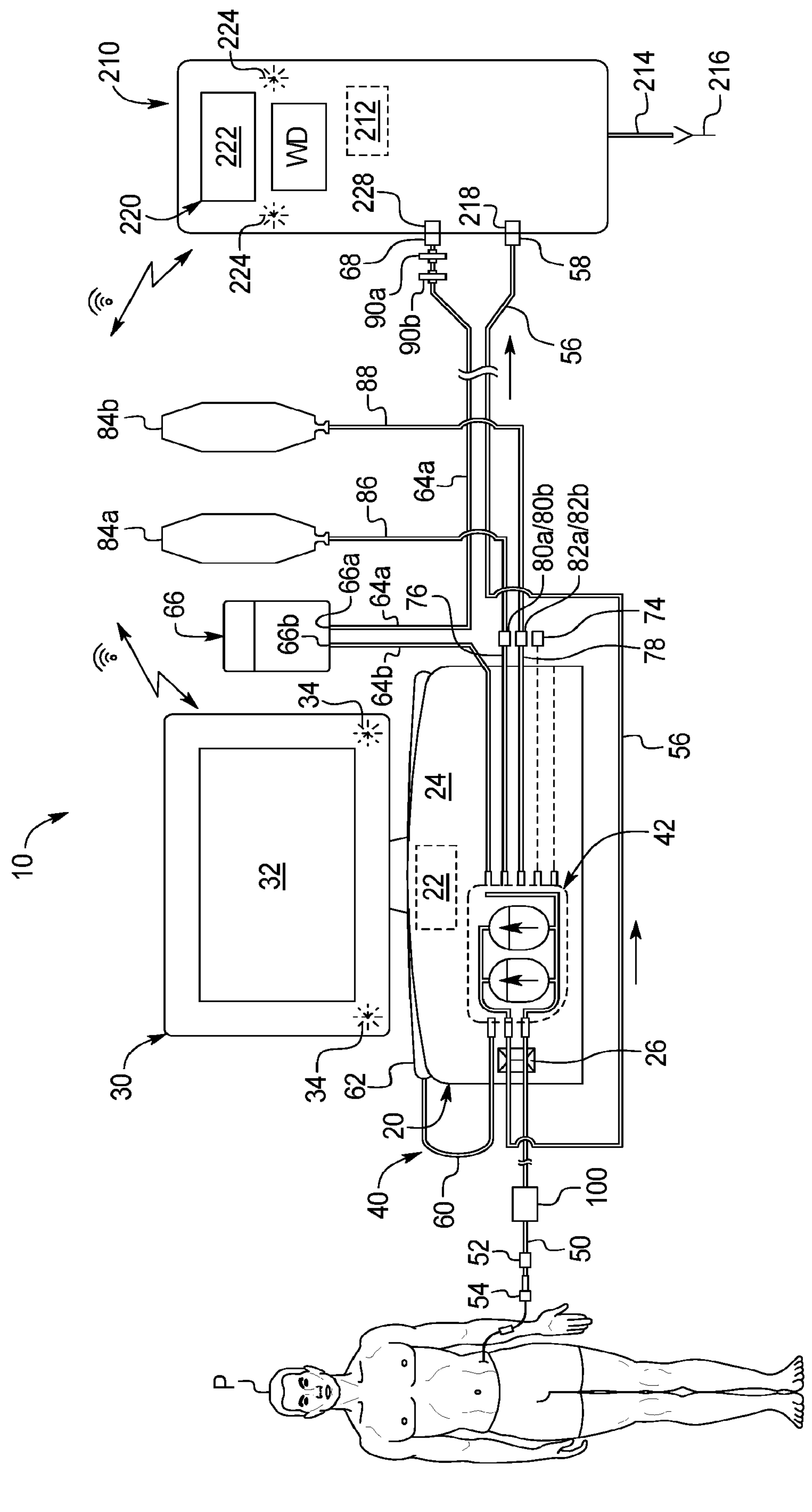
FIG. 1 is a front elevation view of one embodiment of a medical fluid delivery system having point of use dialysis fluid production of the present disclosure.

Referring now to the drawings and in particular to FIG. 1, one embodiment of a peritoneal dialysis system having point of use dialysis fluid production of the present disclosure is illustrated by system 10. System 10 includes a cycler 20 and a water purifier 210. Suitable cyclers for cycler 20 include, e.g., the Amia® or HomeChoice® cycler marketed by Baxter International Inc., with the understanding that those cyclers are provided with updated programming to perform and use the point of use dialysis fluid produced according to system 10. To this end, cycler 20 includes a control unit 22 having at least one processor and at least one memory. Control unit 22 further includes a wired or wireless transceiver for sending information to and receiving information from a water purifier 210. Water purifier 210 also includes a control unit 212 having at least one processor and at least one memory. Control unit 212 further incudes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier 210 includes a drain line 214 leading to a drain 216, which can be a house drain or a drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (ix) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan or tray, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 210 in the illustrated embodiment also includes a user interface 220. Control unit 212 of water purifier 210 in an embodiment includes a video controller, which may have its own processing and memory for interacting with primary control processing and memory of control unit 212. User interface 220 includes a video monitor 222, which may likewise operate with a touch screen overlay placed onto video monitor 222 for inputting commands into control unit 212. User interface 220 may also include one or more electromechanical input device, such as a membrane switch or other button. Control unit 212 may further include an audio controller for playing sound files, such as alarm or alert sounds, at one or more speaker 224 of water purifier 210.

Figure 2:
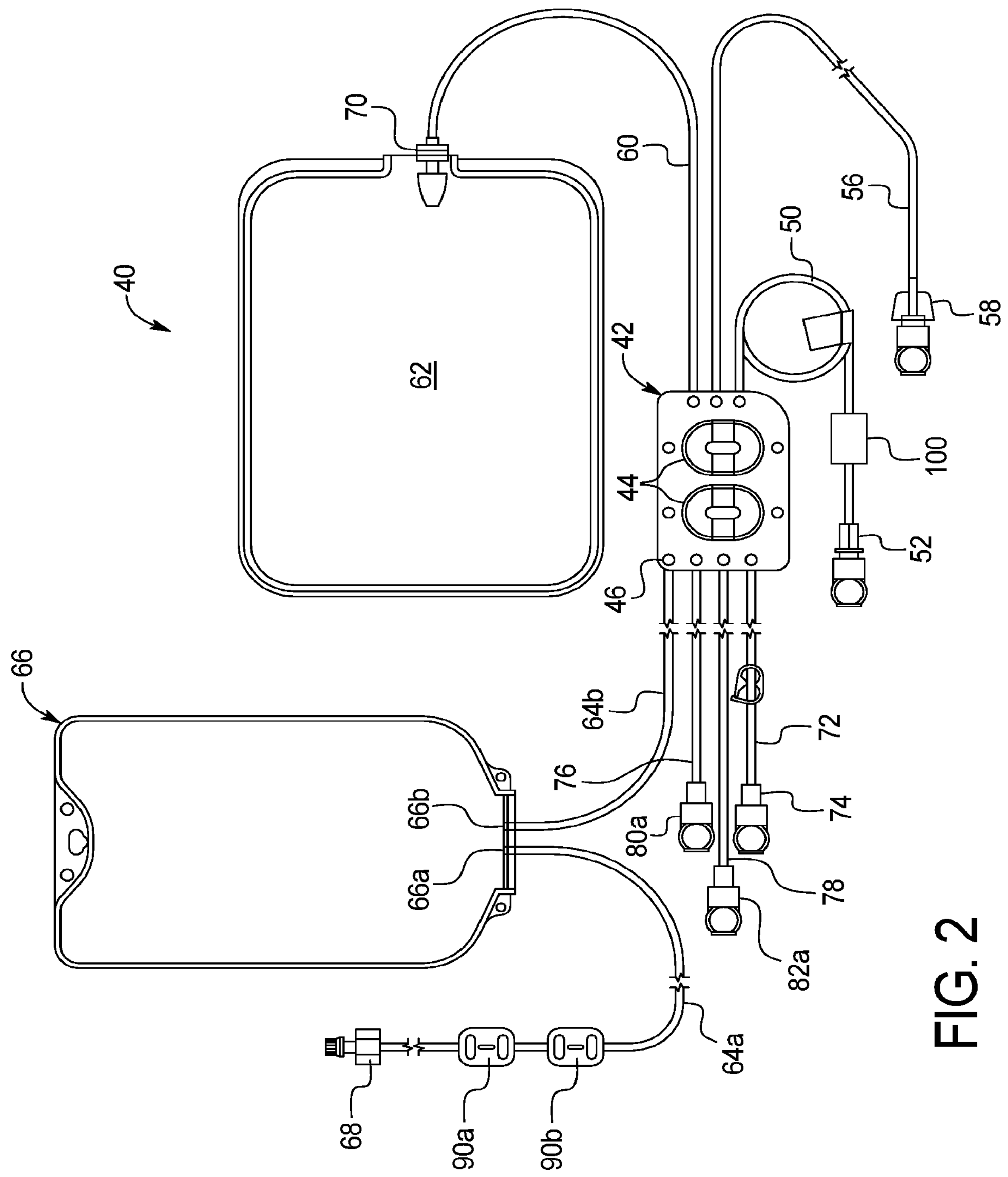
FIG. 2 is an elevation view of one embodiment of a disposable set used with the system illustrated in FIG. 1.

Referring additionally to FIG. 2, one embodiment of disposable set 40 is illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Patient line 50 also includes a sterile sterilizing grade filter 100 discussed in detail below. Disposable set 40 includes a drain line 56 that extends from a drain line port of cassette 42 and terminates at a drain line connector 58. FIG. 1 illustrates that drain line connector 58 connects removeably to a drain connector 218 of water purifier 210.

FIGS. 1 and 2 further illustrate that disposable set 40 includes a heater/mixing line 60 that extends from a heater/mixing line port of cassette 42 and terminates at a heater/mixing bag 62 discussed in more detail below. Disposable set 40 includes an upstream water line segment 64*a* that extends to a water inlet 66*a* of water accumulator 66. A downstream water line segment 64*b* extends from a water outlet 66*b* of water accumulator 66 to cassette 42. In the illustrated embodiment, upstream water line segment 64*a* begins at a water line connector 68 and is located upstream from water accumulator 66. FIG. 1 illustrates that water line connector 68 is removeably connected to a water outlet connector 228 of water purifier 210.

Water purifier 210 outputs water and possibly water suitable for peritoneal dialysis ("WFPD"). Sterile sterilizing grade filter 100 in patient line 50 ensures that any contaminants in the water exiting water purifier 210 are removed. In addition to sterile patient line sterilizing grade filter 100, system 10 may, but does not have to, provide one or more sterile sterilizing grade filter in one or more of the water lines. In the illustrated embodiment, a sterile sterilizing grade filter 90*a* is placed upstream from a downstream sterile sterilizing grade filter 90*b*, respectively. Filters 90*a* and 90*b* may be placed in water line segment 64*a* upstream of water accumulator 66. Sterile sterilizing grade filters 100, 90*a* and 90*b* may be pass-through filters that do not have a reject line. Pore sizes for the filtering membranes of filters 100, 90*a* and 90*b* may, for example, be less than a micron, such as 0.1 or 0.2 micron. Suitable sterile sterilizing grade filters 100, 90*a* and 90*b* may be provided by the assignee of the present disclosure. In an embodiment, only one of upstream or downstream sterilizing filter 90*a* and 90*b* is needed to produce WFPD, nevertheless, two sterile sterilizing grade filters 90*a* and 90*b* may be provided in the illustrated embodiment for redundancy in case one fails.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first, e.g., glucose, concentrate line 76 extending from a first concentrate port of cassette 42 and terminates at a first, e.g., glucose, cassette concentrate connector 80*a*. A second, e.g., buffer, concentrate line 78 extends from a second concentrate port of cassette 42 and terminates at a second, e.g., buffer, cassette concentrate connector 82*a*.

FIG. 1 illustrates that a first concentrate container 84*a* holds a first, e.g., glucose, concentrate, which is pumped from container 84*a* through a container line 86 to a first container concentrate connector 80*b*, which mates with first cassette concentrate connector 80*a*. A second concentrate container 84*b* holds a second, e.g., buffer, concentrate, which is pumped from container 84*b* through a container line 88 to a second container concentrate connector 82*b*, which mates with second cassette concentrate connector 82*a*.

In an embodiment, to begin treatment, patient P loads cassette 42 into cycler 20 and in a random or designated order (i) places heater/mixing bag 62 onto cycler 20, (ii) connects upstream water line segment 64*a* to water outlet connector 228 of water purifier 210, (iii) connects drain line 56 to drain connector 218 of water purifier 210, (iv) connects first cassette concentrate connector 80*a* to first container concentrate connector 80*b*, and (v) connects second cassette concentrate connector 82*a* to second container concentrate connector 82*b*. At this point, patient connector 52 is still capped. Once fresh dialysis fluid is prepared and verified, patient line 50 including sterile sterilizing grade filter 100 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyester ether ("PCCE") and may be of one or more layer. Any of the tubing or lines may be made for example of polyvinyl chloride ("PVC"). Any of the connectors may be made for example of acrylonitrile-butadiene-styrene ("ABS", e.g., a connector 70 of heater/mixing bag or container 62 and/or for concentrate connectors 80*a*, 80*b*, 82*a*, 82*b* discussed below), acrylic (e.g., for drain line connector 58) or PVC (e.g., for water line connector water line connector 68). Any of the bags or containers, such as heater/mixing bag or container 62 discussed below, may be made of PVC. The materials for any of the above components may be changed over time. The housing for sterile sterilizing grade filter 100 may be made of any of the materials listed above.

Control unit 22 may be programmed to cause cycler 20 to perform one or more mixing action to help mix dialysis fluid properly and homogeneously for treatment. For example, any of fluid pump chambers 44 may be caused to withdraw into the pump chambers some amount of mixed fluid (e.g., made from one or both first and second concentrates 84*a*, 84*b* and purified water) from heater/mixing bag 62 and send such mixture back to heater/mixing bag 62 and repeat this procedure multiple times (described herein as a mixing sequence or "waffling"). In particular, to perform a mixing sequence, control unit 22 in an embodiment causes cycler 20 to close all fluid valve chambers 46 at cassette 42 except for the fluid valve chamber 46 to heater/mixing line 60 and heater/mixing bag 62. Fluid pump chambers 44 are stroked sequentially and repeatedly (i) pulling a possibly unmixed fluid combination of purified water and concentrates from heater/mixing bag 62 into the pump chambers, followed by (ii) pushing the mixed purified water and concentrates from the pump chambers back to heater/mixing bag 62 and (iii) repeating (i) and (ii) at least one time. Control unit 22 may be programmed to stroke fluid pump chambers 44 and associated valves 46 together so that they both pull and push at the same time, or alternatingly so that one pump chamber 44 pulls from heater/mixing bag 62, while the other pump chamber 44 pushes to heater/mixing bag 62, creating turbulence in heater/mixing line 60.

Providing container or bag 62 operable with cassette 42 and heater/mixing line 60 enables the purified water from accumulator 66 and the concentrates from first and second concentrate containers 84*a* and 84*b* to at least partially mix before entering the container or bag. Even if cassette 42 is not provided, however, the purified water and at least one concentrate will mix partially in heater/mixing line 60 prior to reaching the container or bag.

Patient Line Filter

Figure 3:
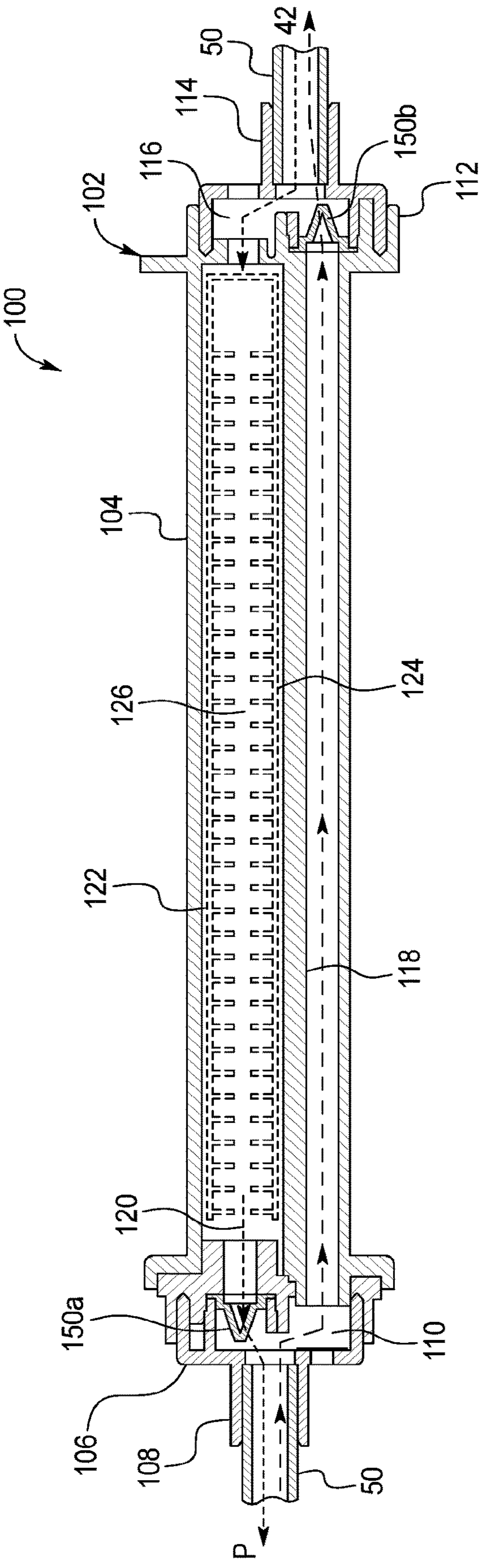
FIG. 3 is an elevation section view of one embodiment of a patient line filter useable with the disposable set of FIG. 2.

Referring now to FIG. 3, a schematic illustration of an embodiment of patient line sterile sterilizing grade filter 100 is illustrated, showing flowpaths taken by fresh dialysis fluid mixed online at the point of use to the patient and used dialysis fluid returning from the patient. In an embodiment, control unit 22 of cycler 20 causes fluid pump chambers 44 and fluid valve chambers 46 of disposable cassette 42 to pump fresh dialysis fluid under positive pressure from right to left in FIG. 3 and from cassette 42 to patient P. Control unit 22 of cycler 20 causes fluid pump chambers 44 and fluid valve chambers 46 of disposable cassette 42 to pump used dialysis fluid under negative pressure fluid from left to right in FIG. 3 and from patient P to cassette 42.

Patient line sterile sterilizing grade filter 100 includes a filter housing 102, any one or more components of which may be made of any of the materials listed above, and which may be made of one or more molded, e.g., injection molded, piece. In the illustrated embodiment, housing 102 includes an elongated enclosure 104 sealed at two ends by a first port cap 106 and a second port cap 112. First port cap 106 includes a first port 108 and defines a first manifold or open area 110, while second port cap 112 includes a second port 114 and defines a second manifold or open area 116. First and second ports 108 and 112 may configured to connect sealingly to segments of patient line 50 via a compression fitting (ports have a compression connector), a hose barb fitting (ports have hose barbs), a luer connection (ports have a male or female luer connector), a stretching of the patient line fitting (outside diameter of the ports is larger than an inner diameter of segments of patient line 50) or combinations thereof.

FIG. 3 illustrates that filter housing 102 in one embodiment forms a used dialysis fluid pathway 118 and houses a fresh dialysis fluid pathway 120. First manifold or open area 110 and second manifold or open area 116 are able to receive both fresh and used dialysis fluids. The line with the arrows pointing to the right indicates used dialysis fluid flowing through used dialysis fluid pathway 118, while the line with the arrows pointing to the left indicates fresh dialysis fluid flowing through fresh dialysis fluid pathway 120. Fresh dialysis fluid pathway 120 as illustrated splits into a first, upper branch 122 and a second, lower branch 124. As illustrated in greater detail below, fresh dialysis fluid flows downwardly from first, upper branch 122 though multiple generally parallel passageways created by a first filter membrane and an inner grid into an interior region 126 of fresh dialysis fluid pathway 120. Similarly, fresh dialysis fluid flows upwardly from second, lower branch 124 though multiple generally parallel passageways created by a second filter membrane and the interior grid into the interior region 126 of fresh dialysis fluid pathway 120.

First port cap 106 houses a first one-way valve 150*a*, which is sealed to the structure forming fresh dialysis fluid pathway 120. Second port cap 112 houses a second one-way valve 150*b*, which is sealed to elongated enclosure 104 of filter housing 102 forming used dialysis fluid pathway 118 in the illustrated embodiment. First and second one-way valves 150*a* and 150*b* may be made of a medically safe rubber or plastic, such as silicone or any of the flexible materials listed above. First and second one-way valves 150*a* and 150*b* may be, for example, duckbill check valves.

As illustrated in FIG. 3, first one-way valve 150*a* is oriented such that it opens under positive pressure of the fresh dialysis fluid delivered through fresh dialysis fluid pathway 120 by pumping cassette 42. Fresh dialysis fluid exiting one-way valve 150*a* flows through first port 108 of first port cap 106 and a segment of patient line 50 to patient P. The orientation of one-way valve 150*a* however is such that valve 150*a* is closed under negative pressure from pumping cassette 42 pulling used dialysis fluid into filter 100 via first port 108 of first port cap 106. In this manner, used dialysis fluid is prevented from entering fresh dialysis fluid pathway 120 and contacting the filter membranes, which is desirable since filtering used dialysis fluid could remove contaminants from the used dialysis fluid, clog the filter membrane, and reintroduce the contaminants into the next cycle of fresh fluid.

As further illustrated in FIG. 3, second one-way valve 150*b* is oriented such that it opens under negative pressure of the used dialysis fluid pulled through used dialysis fluid pathway 118 by pumping cassette 42. Used dialysis fluid exiting one-way valve 150*b* flows through second port 114 of second port cap 112 and a segment of patient line 50 to disposable cassette 42. The orientation of one-way valve 150*b* however is such that valve 150*b* is closed under positive pressure from pumping cassette 42 pushing fresh dialysis fluid into filter 100 via second port 114 of second port cap 112. In this manner, all fresh dialysis fluid is forced to travel through fresh dialysis fluid pathway 120 including its filtering membranes.

Figure 4:
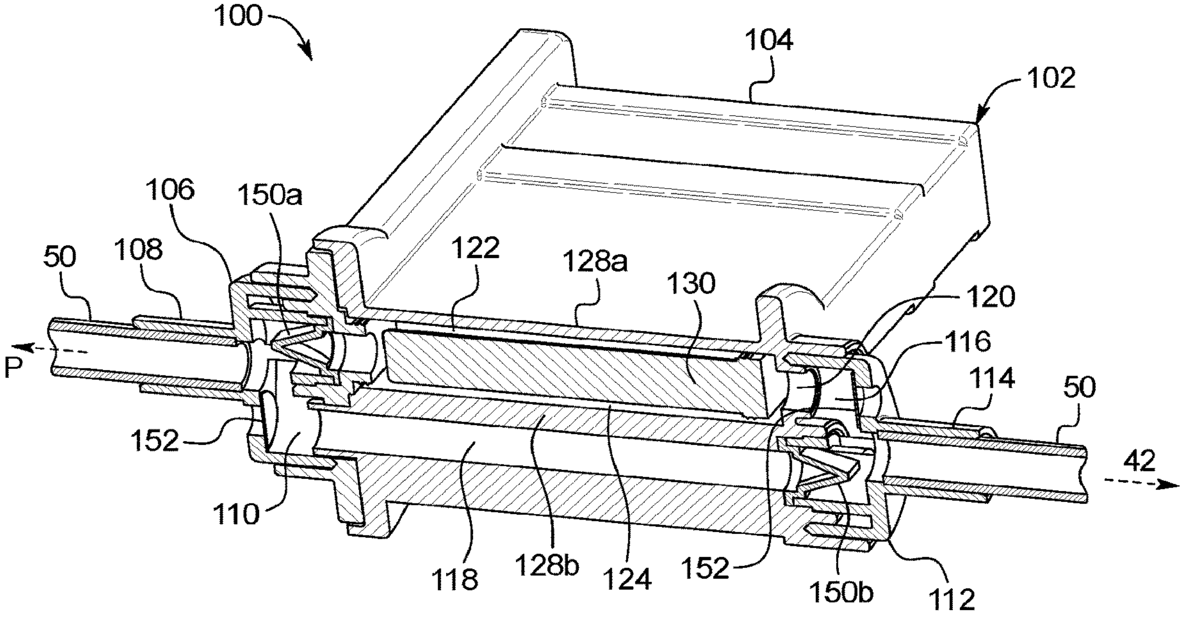
FIG. 4 is a perspective section view of one embodiment of a patient line filter useable with the disposable set of FIG. 2.

Referring now to FIG. 4, patient line sterile sterilizing grade filter 100 is illustrated in more detail. Here, a section is taken through patient line 50, filter housing 102, used dialysis fluid pathway 118, fresh dialysis fluid pathway 120, first port cap 106, second port cap 112 and one-way valves 150*a* and 150*b*. As discussed above, filter housing 102 defines used dialysis fluid pathway 118 and holds one-way valve 150*b* in one embodiment. In FIG. 4, second port cap 112 may also be formed with or sealed to filter housing 102. As referred to herein, "sealed to" may but does not have to mean adhered to, ultrasonically welded to, solvent bonded to, mechanically sealed to, or be any combination thereof.

FIG. 4 illustrates that in one embodiment, the filter membranes, and one-way valve 150*a* may be held by a membrane housing 130 located within and sealed to filter housing 102. Membrane housing 130 may be made of any of the materials discussed herein, may be molded, e.g., injection molded, in one or more piece, and may be sealed to filter housing 102 and first port cap 106 via any of the techniques described herein. In the illustrated embodiment, first port cap 106 is sealed to membrane housing 130. In an alternative embodiment, port cap 106 may be formed with membrane housing 130.

In the illustrated embodiment of FIG. 4, both filter housing 102 and membrane housing 130 take part in forming fresh dialysis fluid pathway 120. Upper branch 122 of fresh dialysis fluid pathway 120 is located between an upper wall 128*a* of filter housing 102 and an upper wall of membrane housing 130 (which houses the upper filter membrane as illustrated below). Lower branch 124 of fresh dialysis fluid pathway 120 is located between a dividing wall 128*b* of filter housing 102 and a lower wall of membrane housing 130 (which houses the lower filter membrane as illustrated below). Interior region 126 of fresh dialysis fluid pathway 120 is located within membrane housing 130.

FIG. 4 better illustrates the structure and orientation of one-way valves 150*a* and 150*b*. One-way valve 150*a* may be sealed to, e.g., adhered to, membrane housing 130 and/or clamped between membrane housing 130 and first port cap 106. In the illustrated embodiment, one-way valve 150*a* is a duckbill check valve with its slitted duckbill angled towards patient P, such that positive fresh dialysis fluid pressure provided by pumping cassette 42 opens the slit from inside the check valve, and such that negative pressure from cassette 42 pumping used dialysis fluid cannot open the slit. One-way valve 150*b* may be sealed to, e.g., adhered to, filter housing 102 and/or clamped between filter housing 102 and second port cap 114 as illustrated. In the illustrated embodiment, one-way valve 150*b* is also a duckbill check valve with its slitted duckbill angled instead towards pumping cassette 42, such that negative used dialysis fluid pressure provided by pumping cassette 42 opens the slit from outside the check valve, and such that positive pressure from cassette 42 pumping fresh dialysis fluid cannot open the slit.

FIG. 4 also illustrates that elongated enclosure 104 of filter housing may include, e.g., be sealed to, one or more hydrophobic (air passing but liquid retaining) vents 152. Hydrophobic vents 152 allow air to escape sterile sterilizing filter 100, e.g., during priming and prior to treatment. Removing air from sterile sterilizing filter 100 helps to prevent air from reaching patient P. The air removal also helps to protect hydrophilic membranes 140 and 142.

Figure 5:
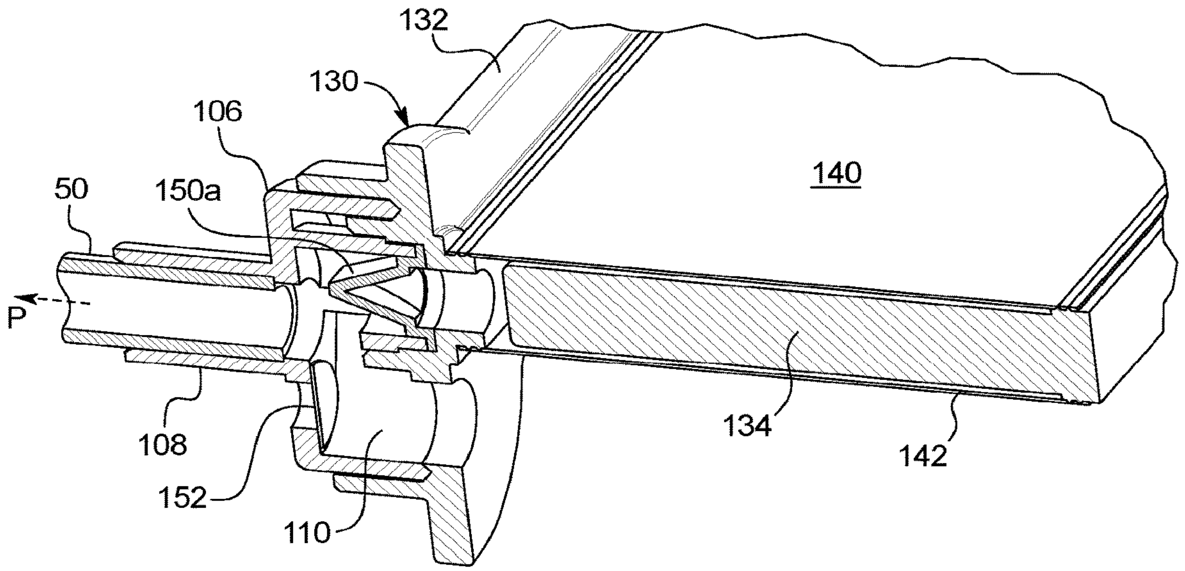
FIG. 5 is a perspective section view of one embodiment of a patient line filter useable with the disposable set of FIG. 2, in which the filter housing has been removed to better show an embodiment of the filter membranes.

Referring now to FIG. 5, membrane housing 130 is shown in more detail with filter housing 102 having been cutaway. Membrane housing 130 includes a mounting arm 132 sized and arranged to be sealed to filter housing 102 and first port cap 106 via any of the techniques discussed above. Mounting arm 132 is also sized and arranged to be sealed, e.g., adhered, to one-way valve 150*a*. Mounting arm 132 extends to a grid housing 134 shown in more detail below in connection with FIG. 6. Importantly in FIG. 5, grid housing 134 is illustrated as being sealed to upper and lower (first and second) filter membranes 140 and 142. First, upper membrane 140 filters fresh dialysis fluid flowing downwardly through first, upper branch 122, while second lower membrane 142 filters fresh dialysis fluid flowing upwardly through second, lower branch 124.

Filter membranes 140 and 142 are each hydrophilic membranes in one embodiment. Hydrophilic membranes in general allow liquid water to pass from one side of the membrane to the other and when properly wetted block air from such passing. Pore sizes for filter membranes 140 and 142 may, for example, be less than a micron, such as 0.1 or 0.2 micron. This pore size helps to remove any lingering contaminants or impurities in the fresh dialysis fluid from any of: the purified water used to make the fresh dialysis fluid, the concentrates used to make the fresh dialysis fluid, and/or any portion of disposable set carrying the purified water or concentrates to patient P.

Figure 6:
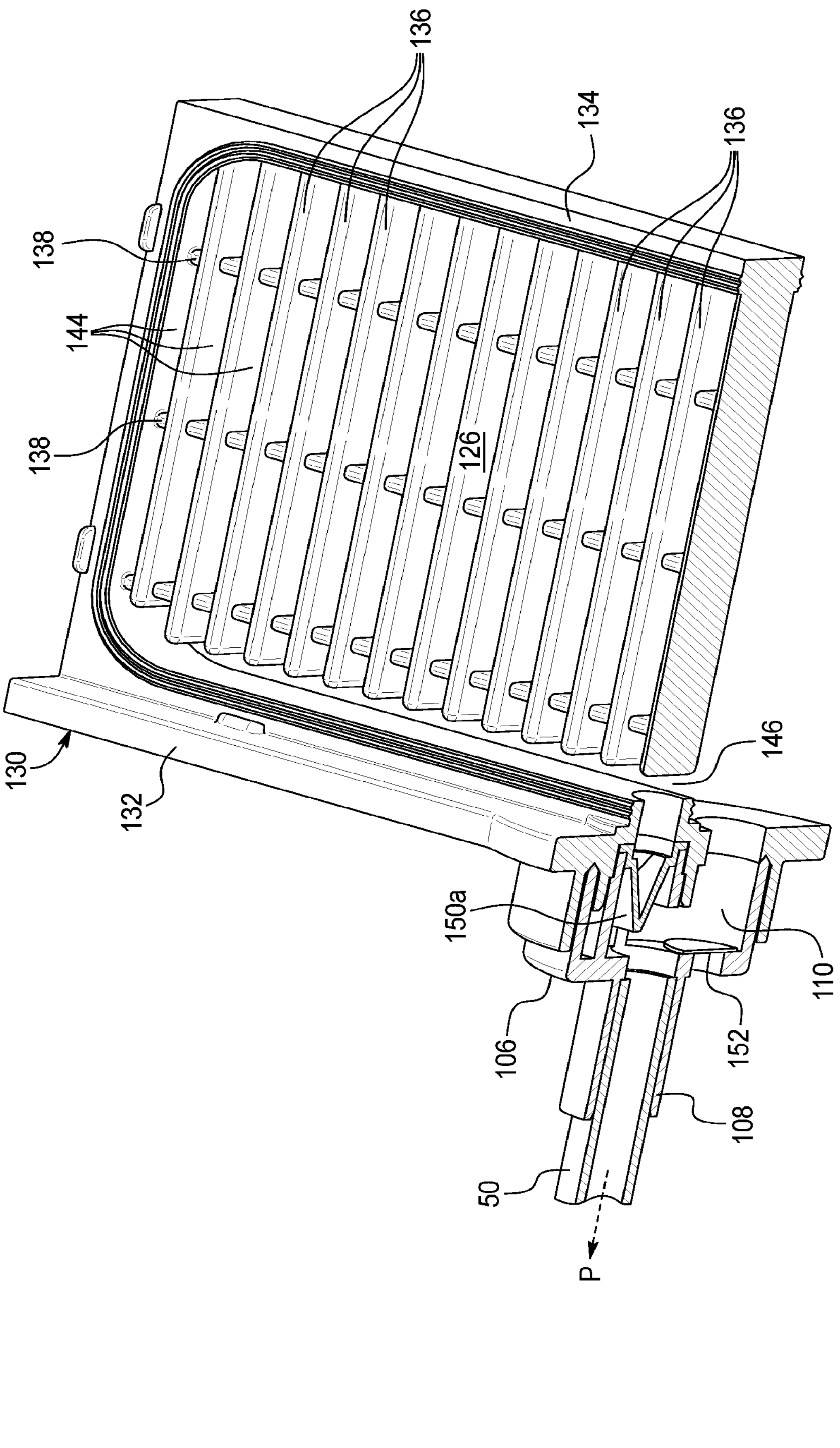
FIG. 6 is a perspective section view of one embodiment of a patient line filter useable with the disposable set of FIG. 2, in which the filter housing and filter membranes have been removed to better show an embodiment of the a spacer grid located between the filter membranes.

Referring now to FIG. 6, membrane housing 130 discussed in connection with FIG. 5 is illustrated in more detail having filter membranes 140 and 142 removed, so that interior region 126 of fresh dialysis fluid pathway 120 inside membrane housing 130 may be viewed. In particular, grid housing 134 is illustrated in more detail. Grid housing 134 may be made (e.g., injection molded) from any of suitable material discussed herein. In the illustrated embodiment, grid housing 134 extends from mounting arm 132 of membrane housing 130. Grid housing 134 includes a plurality of baffles 136 that extend across grid housing 134 and separate filtered dialysis fluid that has flowed through filter membranes 140 and 142 into plural fluid channels 144 forming interior region 126 of fresh dialysis fluid pathway 120. Baffles 136 help support the thin filter membranes 140 and 142 and space the membranes a desired distance apart.

To maintain baffles 136 in their illustrated separated and generally parallel relationship, plural cross-braces 138 may be provided. Cross-braces 138 are sized (narrowed) to enable filtered dialysis fluid to flow along channels 144 defined by baffles 136, over the cross-braces, to a collection channel 146. Collection channel 146 in turn funnels the filtered dialysis fluid to first one-way valve 150*a*, after which the filtered dialysis fluid exits filter 100 into a downstream segment of patient line 50 as has been discussed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, fluid pump chambers 44 may be pneumatically actuated pump chambers or be a section of peristaltic pumping tube. Similarly, valve chambers 46 may be pneumatically actuated, e.g., be volcano valves, or be sections of tubing operated upon by pinch valves. Likewise, the pump and valve actuators may be pneumatic actuators or be electromechanical actuators, e.g., a peristaltic pump actuator and pinch valves, respectively.

The invention is claimed as follows:

1. A peritoneal dialysis system comprising:
a cycler configured to pump peritoneal dialysis fluid; and
a disposable set configured to receive the peritoneal dialysis fluid pumped by the cycler, the disposable set including a filter having:
a fresh peritoneal dialysis fluid pathway,
a one-way valve located at or near an exit end of the fresh peritoneal dialysis fluid pathway,
a used peritoneal dialysis fluid pathway placed in parallel with the fresh peritoneal dialysis fluid pathway, and
a membrane located along the fresh peritoneal dialysis fluid pathway and configured to filter the peritoneal dialysis fluid,
wherein the one-way valve is configured such that (i) fresh peritoneal dialysis fluid is directed to flow from the cycler towards a patient through the membrane via the fresh peritoneal dialysis fluid pathway, and (ii) used peritoneal dialysis fluid is directed to bypasses the membrane via the used peritoneal dialysis fluid pathway.

2. The peritoneal dialysis system of claim 1, wherein the disposable set includes a line extending from the filter to a connector configured to connect to a patient transfer set.

3. The peritoneal dialysis system of claim 1, wherein the disposable set further includes a disposable drain line.

4. The peritoneal dialysis system of claim 1, wherein the filter is connected to a patient line extending from the cycler.

5. The peritoneal dialysis system of claim 1, wherein the one-way valve is positioned and arranged to prevent the used peritoneal dialysis fluid returning from the patient from reaching the membrane.

6. The peritoneal dialysis system of claim 1, wherein the one-way valve is positioned and arranged to prevent the fresh peritoneal dialysis fluid from flowing through the filter via the used peritoneal dialysis fluid pathway.

7. The peritoneal dialysis system of claim 1, wherein the membrane is housed in a membrane housing located along the fresh peritoneal dialysis fluid pathway, and wherein the filter is configured such that the fresh peritoneal dialysis fluid flows from outside the membrane housing, through the membrane, and into an interior region of the membrane housing.

8. The peritoneal dialysis system of claim 1, wherein the filter includes a housing having a first port and a second port, the first port opening to a first end of the filter housing and the second port opening to a second end of the filter housing, the first end of the filter housing forming a first end of the fresh and used peritoneal dialysis fluid pathways, and the second end of the filter housing forming a second end of the fresh and used peritoneal dialysis fluid pathways.

9. The peritoneal dialysis system of claim 8, wherein the first end of the fresh peritoneal dialysis fluid pathway at the first end of the filter housing corresponds to the exit end of the fresh peritoneal dialysis fluid pathway, and wherein the second end of the used peritoneal dialysis fluid pathway at the second end of the filter housing includes a second one-way valve.

10. The peritoneal dialysis system of claim 1, wherein the membrane is housed in a membrane housing, and wherein the fresh peritoneal dialysis fluid entering the filter flows to an outside of the membrane housing, and fresh, filtered peritoneal dialysis fluid exiting the filter flows from an inside of the membrane housing.

11. The peritoneal dialysis system of claim 1, wherein the membrane is a first membrane, wherein the filter includes a second membrane, wherein the first and second membranes are housed in a membrane housing, and wherein the fresh peritoneal dialysis fluid entering the filter is split into a first branch flowing to an outside of the first membrane and a second branch flowing to an outside of the second membrane.

12. The peritoneal dialysis system of claim 11, wherein the membrane housing includes a grid of passageways located between the first and second membranes.

13. The peritoneal dialysis system of claim 11, wherein the first and second membranes are located on opposing sides of the membrane housing, respectively, the first branch extending to a first side of the membrane housing and the second branch extending to a second side of the membrane housing.

14. The peritoneal dialysis system of claim 1, further comprising at least one hydrophobic vent for removing air from the filter.

15. A peritoneal dialysis system comprising:

a cycler configured to pump peritoneal dialysis fluid; and a disposable set configured to receive the peritoneal dialysis fluid pumped by the cycler, the disposable set including a filter in which the peritoneal dialysis fluid is intended to flow in first and second directions, wherein the filter is configured to filter the peritoneal dialysis fluid flowing in the first direction and to not filter the peritoneal dialysis fluid flowing in the second direction, the filter including:

a filter housing, a first fluid pathway provided by the filter housing for flowing the peritoneal dialysis fluid in the first direction, a one-way valve located at or near an exit end of the first fluid pathway, a second fluid pathway provided by the filter housing for flowing the peritoneal dialysis fluid in the second direction, and a membrane positioned along the first fluid pathway upstream from the one-way valve to filter the peritoneal dialysis fluid flowing in the first direction, wherein the exit end of the first fluid pathway is located downstream from the peritoneal dialysis fluid flow through the membrane.

16. The peritoneal dialysis system of claim 15, wherein the membrane is housed in a membrane housing located within the filter housing and along the first fluid pathway, and wherein the filter is configured such that the peritoneal dialysis fluid flows from outside the membrane housing, through the membrane, and into an interior region of the membrane housing.

17. The peritoneal dialysis system of claim 15, wherein the filter housing includes a first port and a second port, the first port opening to a first end of the filter housing and the second port opening to a second end of the filter housing, the first end of the filter housing forming a first end of the first and second fluid pathways, and the second end of the filter housing forming a second end of the first and second fluid pathways.

18. The peritoneal dialysis system of claim 15, wherein the membrane is housed in a membrane housing located within the filter housing, and wherein the peritoneal dialysis fluid entering the filter flows to an outside of the membrane housing, and filtered peritoneal dialysis fluid exiting the filter flows from an inside of the membrane housing.

19. The peritoneal dialysis system of claim 15, wherein the membrane is a first membrane, and wherein the filter includes a second membrane, wherein the first and second membranes are housed in a membrane housing located within the filter housing, and wherein the peritoneal dialysis fluid entering the filter is split into a first branch flowing to an outside of the first membrane and a second branch flowing to an outside of the second membrane.

* * * * *